(12) United States Patent
Otsubo

(10) Patent No.: US 8,147,470 B2
(45) Date of Patent: *Apr. 3, 2012

(54) PANTS-TYPE DIAPER

(75) Inventor: Toshifumi Otsubo, Kanonji (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/767,205

(22) Filed: Apr. 26, 2010

(65) Prior Publication Data
US 2010/0211036 A1 Aug. 19, 2010

Related U.S. Application Data

(62) Division of application No. 11/923,304, filed on Oct. 24, 2007, now Pat. No. 7,722,734.

(30) Foreign Application Priority Data

Nov. 15, 2006 (JP) .................. 2006-309655

(51) Int. Cl.
A61F 13/15 (2006.01)
(52) U.S. Cl. ....... 604/385.101; 604/385.19; 604/385.01; 604/385.21; 604/385.25
(58) Field of Classification Search ........... 604/385.101, 604/385.25
See application file for complete search history.

(56) References Cited

U.S. PATENT DOCUMENTS

| | | | |
|---|---|---|---|
| 3,926,189 A | 12/1975 | Taylor | |
| 4,573,990 A | 3/1986 | Ohsaki | |
| 5,531,730 A * | 7/1996 | Dreier | 604/385.19 |
| 5,554,142 A | 9/1996 | Dreier et al. | |
| 6,409,711 B1 | 6/2002 | Jonbrink | |
| 6,508,798 B1 | 1/2003 | Widlund et al. | |
| 6,648,868 B2 | 11/2003 | Sayama et al. | |
| 6,824,534 B2 | 11/2004 | Mishima et al. | |
| 7,763,002 B2 * | 7/2010 | Otsubo | 604/385.101 |

FOREIGN PATENT DOCUMENTS

JP 2002-011044 A 1/2002

* cited by examiner

*Primary Examiner* — John L. Goff
*Assistant Examiner* — Barbara J. Musser
(74) *Attorney, Agent, or Firm* — Lowe, Hauptman, Ham & Berner, LLP

(57) ABSTRACT

The present invention provides a disposable pants-type diaper including on a crotch region thereof a separator adapted to prevent feces from coming in contact with the wearer's skin. A basic structure has the crotch region, which is provided with a folded sheet piece attached thereto so as to form the separator. The folded sheet piece is obtained by folding back the sheet piece along a first transverse center line thereof to define a first half and a second half placed upon each other and bonding end edges of these two halves to each other at responsive middles of these end edges in a transverse direction. With the first transverse center line brought close to a second transverse center line, the folded sheet piece is placed upon the crotch region and the lateral edges of the first half are bonded to the crotch region while a region of the first half defined by the lateral edges is kept to be spaced from the crotch region. Then, the basic structure is folded back along the second transverse center line and the inner surface of the basic structure is bonded to the outer surface of the lateral edges of the second half while a region of the second half defined between the lateral edges is kept to be spaced from the crotch region. Of the basic structure folded back in this manner, the front and rear waist regions are bonded along the lateral edges to make the basic structure in a pants-shape.

10 Claims, 6 Drawing Sheets

PANTS-TYPE DIAPER

RELATED APPLICATIONS

This is a Divisional Application of U.S. application Ser. No. 11/923,304 now U.S. Pat. No. 7,722,734, filed on Oct. 24, 2007, which is based on, and claims priority from, Japan Application Number 2006-309655, filed Nov. 15, 2006. The disclosures of all above applications are hereby incorporated by reference herein in their entirety.

BACKGROUND OF THE INVENTION

The present invention relates generally to a method for making a disposable pants-type diaper and the pants-type diaper obtained by this method, and particularly to the method for making the pants-type diaper adapted to prevent feces from coming in contact with the wearer's skin and such pants-type diaper.

Disposable diapers adapted to prevent feces from coming in contact with and thereby soiling the wearer's skin is well known. For example, the pants-type diaper disclosed in Japanese Unexamined Patent Application Publication No. 2002-11044 (Reference) has a skin contactable sheet provided on a topsheet and a crotch region of this skin contactable sheet is formed with an opening around which an elastic member is in its stretched state to the skin contactable sheet. This opening is exactly opposed to the wearer's anus so that feces discharged by the wearer may move through the opening into a space underlying the skin contactable sheet without an anxiety that feces might come in the wearer's skin.

The diaper disclosed in Reference is not free from the possibility that feces might move into a space between the wearer's skin and the skin contactable sheet and significantly soil the wearer's skin unless the opening formed in the skin contactable sheet is exactly opposed to the wearer's anus. Specifically, it is essential for this known diaper to bring the opening of the skin contactable sheet in line with the anus in the course of putting the diaper on the wearer. However, it can not be determined from the exterior whether the opening of the diaper having been put on the wearer is exactly opposed to the anus or not. Furthermore, the skin contactable sheet is formed with a notch through which urine can be directly absorbed by the absorbent core. However, urine has passed through the notch will be inevitably mixed with feces on the surface of the absorbent core. Liquidity of feces will increase when it is mixed with urine and consequentially a possibility that the wearer's skin might be soiled with feces will correspondingly increase.

SUMMARY OF THE INVENTION

In view of the problem of the conventional diaper as has been described above, it is an object of the present invention to provide a novel disposable pants-type diaper facilitating the wearer's anus to oppose the feces receiving space exactly and thereby protecting the wearer's skin from being contaminated with feces.

According to the present invention, there is provided a method for making a disposable pants-type diaper basically comprising the steps of preparing a basic structure having a crotch region having a back-and-forth direction and a transverse direction which is orthogonal to the back-and-forth direction, a front waist region extending forward from the crotch region and a rear waist region extending rearward from the crotch region, bonding the front and rear waist regions to each other along lateral edges of the front and rear waist regions to make the basic structure in a pants-shape and providing the basic structure on an inner surface thereof with a sheet piece forming a separator adapted to prevent feces from coming in contact with the wearer' skin.

The present invention further comprises the steps of: preparing the sheet piece divided by a first transverse center line bisecting the sheet piece in the back-and-forth direction before attached to the inner surface; folding back the sheet piece along a fold line defined by the first transverse center line so as to place the first and second halves upon each other; bonding the first and second halves placed upon each other in this manner to each other at respective middles of ends of the sheet piece extending in parallel to the first transverse center line to form a folded sheet piece having the first and second halves spaced from each other in regions thereof other than the middles; bringing the first transverse centerline of the folded sheet piece close to a second transverse center line bisecting a dimension of the basic structure in the longitudinal direction and spacing the respective ends of the first and second halves farther than the first transverse center line from the second transverse center line so as to place the first half on the inner surface of front or rear section of the crotch region in the basic structure; bonding the outer surface of the lateral edges of the first half extending in the back-and-forth direction to the inner surface while a region defined between the lateral edges is kept to be spaced from the inner surface; coating the outer surface of the lateral edges of the second half extending in the back-and-forth direction with adhesive; folding back the basic structure along the second transverse center line to bond the inner surface of the basic structure to the outer surface of the lateral edges of the second half by means of the adhesive while the region defined between the lateral edges is spaced from the inner surface; and bonding the respective inner surfaces of the lateral edges of the front and rear waist regions placed upon each other in the basic structure to each other and thereby obtaining the separator from the sheet piece.

According to one preferred embodiment of the present invention, the inner surface of the basic structure placed upon the outer surface of the lateral edges when the basic structure is folded back along the second transverse center line is coated with the adhesive instead of coating the respective outer surfaces of the second half with the adhesive.

According to another preferred embodiment of the present invention, a dimension of the folded sheet piece in the transverse direction is larger than a dimension of the diaper's basic structure in the transverse direction in the region of the folded sheet piece on which the first half is placed.

The present invention relates also to a disposable pants-type diaper obtained by the method.

The method according to the present invention for making the disposable pants-type diaper comprises the steps of bonding the lateral edges of the folded sheet piece having the first and second halves to the inner surface of the crotch region in the basic structure, and then folding back the basic structure along the second transverse center line so that the inner surface of the basic structure is bonded to the lateral edges of the folded sheet piece and, at the same time, the lateral edges of the basic structure in the front and rear waist regions, respectively, are bonded together. In this way, a pants-shaped absorbent chassis is obtained from the basic structure, a pocket-like bodily waste receiving space adapted to receive urine discharged by the wearer is formed between the front section of the crotch region in the basic structure and the folded sheet piece and the pocket-like bodily waste receiving space adapted to receive feces is formed between the rear section of the crotch region in the basic structure and the folded sheet piece. In these bodily waste receiving spaces, the front and rear end edges of the folded sheet piece integrated together on the longitudinal center line of the diaper are kept in contact with the inner sides of the wearer's legs while the crotch region of the basic structure is kept to be spaced from these front and rear end edges. Consequentially, it is assured that the respective bodily waste receiving spaces always open upward and reliably receive urine and feces, respectively, independently of a manner in which the diaper is put on the wearer. The folded sheet piece defining such bodily waste receiving spaces functions as the separator adapted to protect the wearer's skin from coming in contact with urine and feces.

Effects obtained from preferred embodiments of the method according to the present invention for making the pants-type diaper and effects obtained from the pants-type diaper according to the present invention will be described below in details.

DETAILED DESCRIPTION OF THE PREFERRED EMBODIMENTS

Details of a method for making a disposable pants-type diaper according to the present invention will be more fully understood from the description made hereunder with reference to the accompanying drawings.

Figure 1:
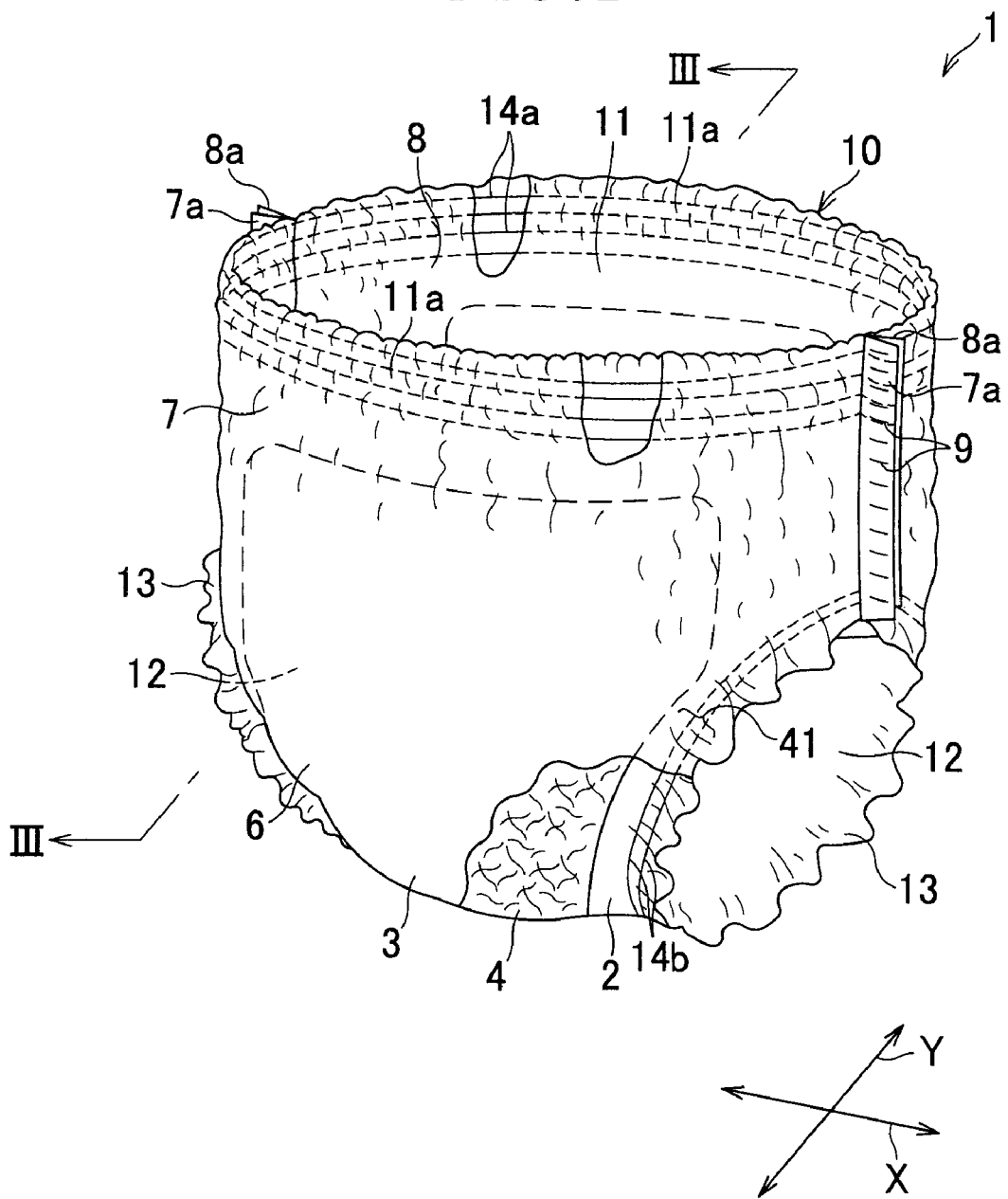
FIG. 1 is a partially cutaway perspective view of a pants-type diaper.

FIG. 1 is a partially cutaway perspective view showing a disposable pants-type diaper 1 obtained by a method according to the present invention for making the same as put on the wearer's body. The pants-type diaper 1 has a pants-shaped absorbent chassis 10 having a bodyside and non-bodyside, comprising a liquid-previous bodyside liner 2, a liquid-impervious outer sheet 3 and a body fluid absorbent core 4 sandwiched between these two sheets 2, 3. The absorbent chassis 10 is configured to define a front waist region 7, a rear waist region 8 and a crotch region 6 extending between the front and rear waist regions 7, 8. The front and rear waist regions 7, 8 are overlapped with each other along respective lateral edges 7a, 8a of thereof and sealed together at a plurality of joint spots 9 arranged along these lateral edges intermittently in a vertical direction as viewed in FIG. 1 so as to form a waist-hole 11 and a pair of leg-holes 12. Sandwiched between the bodyside liner 2 and the outer sheet 3, a plurality of waist elastic members 14a circumferentially extend along a periphery defining the waist-hole 11a and are bonded in a stretched state between the bodyside liner 2 and the outer sheet 3. In a similar manner, a plurality of leg elastic members 14b sandwiched between the bodyside liner 2 and the outer sheet 3 circumferentially extend along each periphery 13 defining each of the leg-holes 12 and are bonded in a stretched state between the bodyside liner 2 and the outer sheet 3 so that these leg elastic members 14b, bodyside liner 2 and outer sheet 3 may form annular elastic portions 41 around the respective legs.

Figure 2:
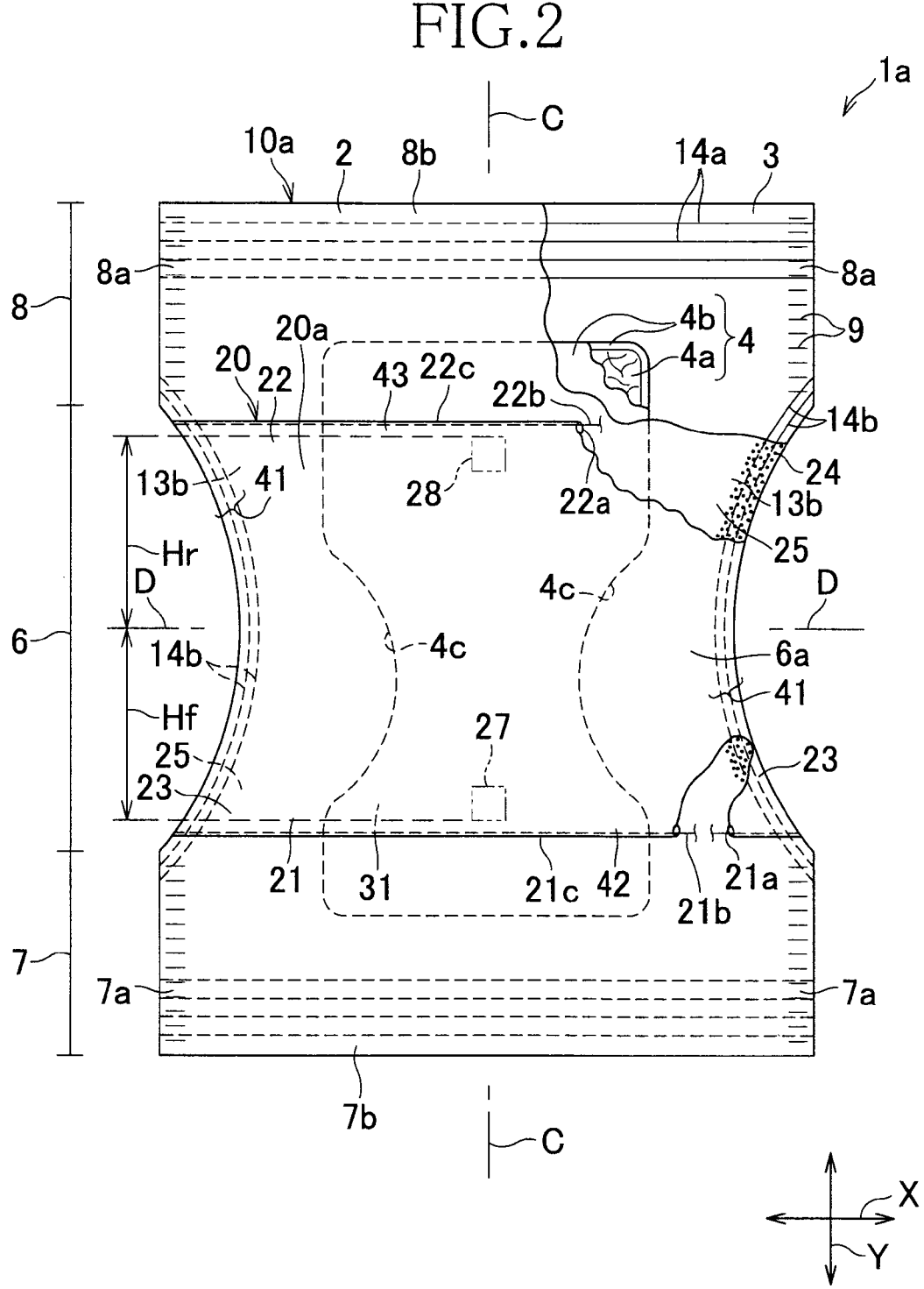
FIG. 2 a plan view showing the pants-type diaper having front and rear waist regions peeled from each other, developed and flattened.

FIG. 2 is a partially cutaway plan view showing a developed diaper 1a corresponding to the diaper 1 of FIG. 1 having the front and rear waist regions 7, 8 peeled off from each other at the joint spots 9 and then fully developed in a transverse direction indicated by a double-headed arrow X as well as in a back-and-forth direction indicated by a double-headed arrow Y which is orthogonal to the transverse direction. FIG. 2 shows an inner side of such developed diaper 1a. In the developed diaper 1a, the absorbent chassis 10 corresponds to an hourglass-shaped basic structure 10a. The periphery 11a of the waist-hole 11 in FIG. 1 corresponds, in FIG. 2, to a front end 7b and a rear end 8b of the basic structure 10a while the peripheries 13 of the respective leg-holes 12 correspond, in FIG. 2, to lateral edges 13b of the crotch region of the basic structure 10a. While these lateral edges 13b curve toward a longitudinal center line C-C bisecting a width of the basic structure 10a, the lateral edges 7a, 8a of the front and rear waist regions 7, 8, respectively, extend in the back-and-forth direction Y substantially in parallel to the longitudinal center line C-C. The core 4 also is generally hourglass-shaped and comprises a mixture 4a of fluff pulp fibers and super-absorbent polymer particles wrapped with a covering sheet 4b having a high absorbability as a well as a high spreadability for body fluids such as tissue paper. In the basic structure 10a, the bodyside liner 2 is provided with a separator 20 formed of a sheet piece 20a which is hydrophobic, preferably hydrophobic and liquid-impervious. Such developed diaper 1a is configured symmetrically about the longitudinal center line C-C as well as about a transverse center line D-D which is orthogonal to the longitudinal center line C-C.

The separator 20 has lateral edges 23 fixed to the lateral edges 13b of the crotch region, respectively, by means of hot melt adhesive 24, a front end edge 21 lying in the crotch region 6 aside toward the front waist region 7 so as to extend in the transverse direction X to the respective lateral edges 13b of the crotch region 6 and a rear end edge 22 lying in the crotch region 6 aside toward the rear waist region 8 so as to extend in the transverse direction X to the respective lateral edges 13b of the crotch region 6. Except for the lateral edges 23, the separator 20 is substantially free from the bodyside liner 2 so that a tunnel- or pocket-like bodily waste receiving space 31 (See FIG. 3) can be defined between the separator 20 and the bodyside liner 2. The front end edge 21 and the rear end edge 22 respectively have sleeves 21a, 22a formed by folding back the respective end edges 21, 22 of the separator 20. These sleeves 21a, 22a respectively contain a front elastic member 21b and a rear elastic member 22b attached in a stretched state thereto to form a front elastic portion 42 and a rear elastic portion 43, respectively, extending between the lateral edges 13b of the crotch region 6. These elastic portions 42, 43 intersect with elastic portions 41 formed by the leg elastic members 14b, the bodyside liner 2 and the outer sheet 3 in the basic structure 10a. The front end edge 21 and the rear end edge 22 are substantially at equal distances Hf, Hr from a transverse center line D-D and respectively include a front joint portion 27 and a rear joint portion 28 indicated by imaginary lines on the longitudinal center line C-C.

Figure 3:
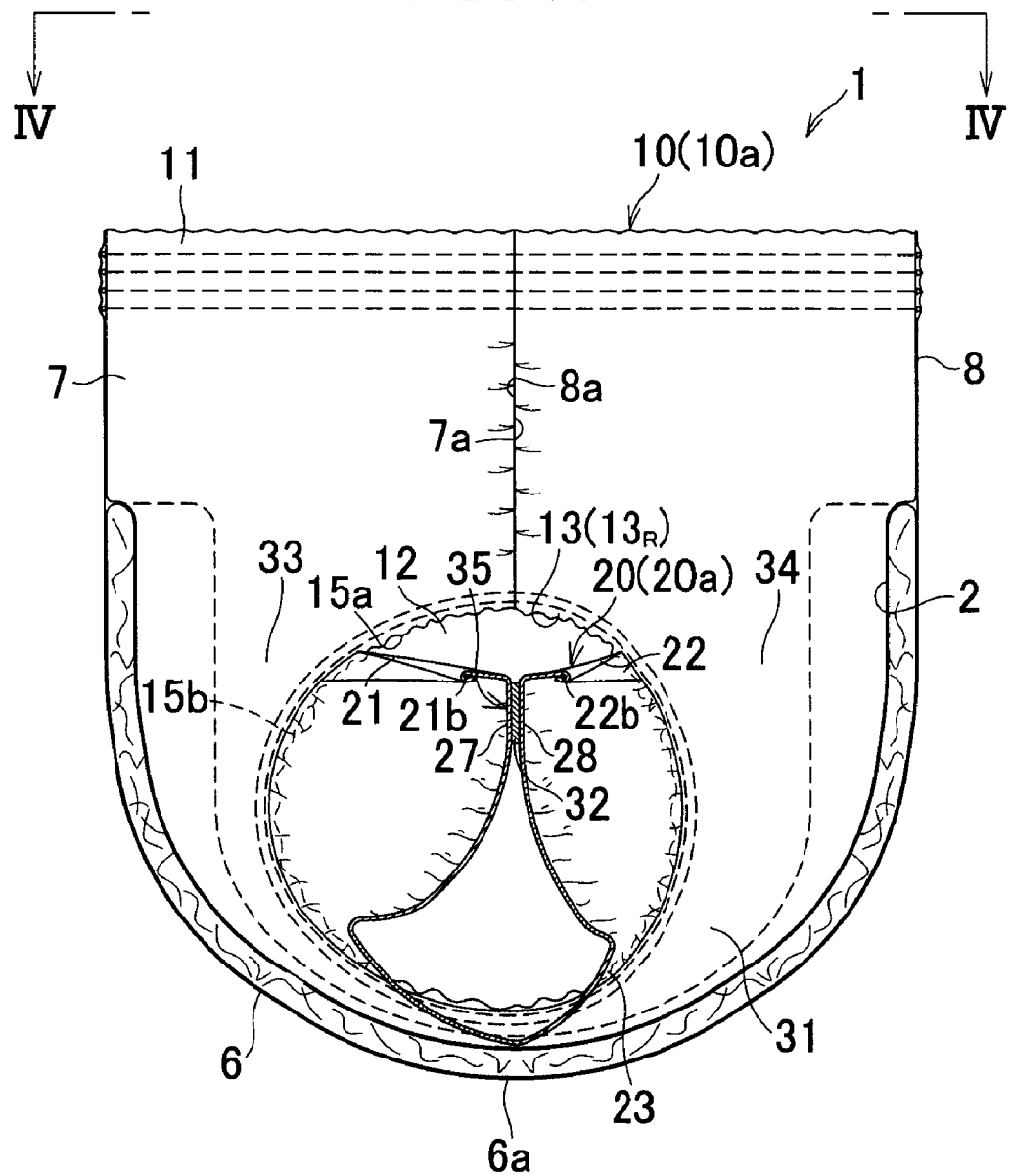
FIG. 3 is a sectional view taken along the line III-III in FIG. 1.

FIG. 3 is a sectional view taken along the line III-III in FIG. 1 wherein the line III-III conforms to the longitudinal center line C-C. The absorbent chassis 10 includes the front waist region 7 and the rear waist region 8 joined together along the lateral edges 7a, 8a, respectively. The crotch region 6 shown in FIG. 2 now bows in FIG. 3 generally in a U-shape and the lateral edges 13b of the crotch region 6 now appear as the peripheries 13 defining the respective leg-holes 12. The separator 20 appears in FIG. 3 as having a joint region 35 in which the front end edge 21 and the rear end edge 22 of the separator 20 are permanently bonded together by means of a bond 32 such as hot melt adhesives or pressure-sensitive adhesives. The bodily waste receiving space 31 defined by the separator 20 and the bodyside liner 2 has a front opening 33 defined by the front end edge 21 together with the bodyside liner 2 and a rear opening 34 defined by the rear end edge 22 together with the bodyside liner 2. At a bottom 6a defined by a lowest portion of the crotch region 6, the bodyside liner 2 and the separator 20 are substantially or really in contact with each other.

Figure 4:
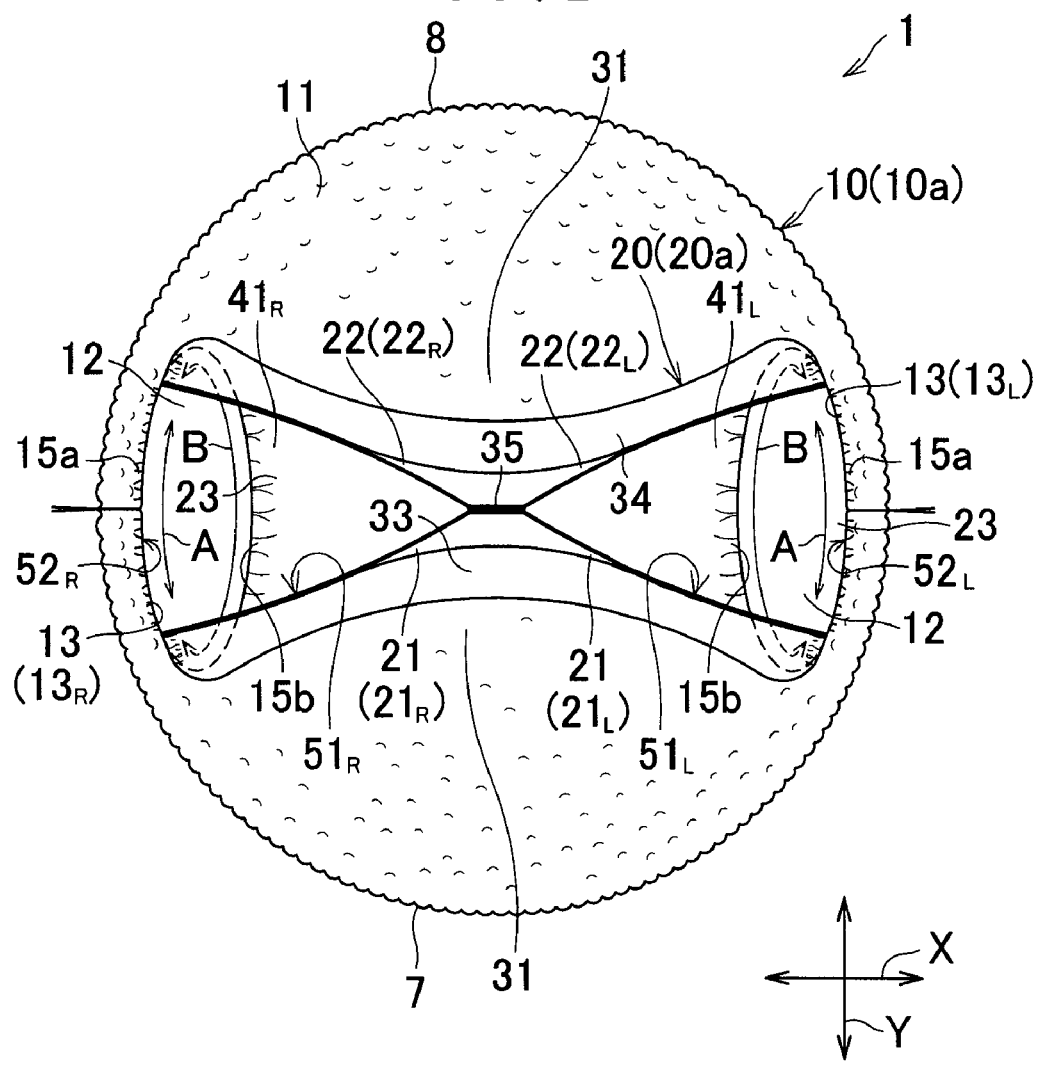
FIG. 4 is an overhead view of the pants-type diaper as viewed in the direction indicated by the arrow line IV-IV in FIG. 3.

FIG. 4 is an overhead view of the diaper 1 as viewed in a direction indicated by the arrowed line IV-IV in FIG. 3, i.e., as viewed from above the waist-hole 11. The front end edge 21 of the separator 20 has its dimension in the transverse direction X bisected by the joint portion 35 into a front end segment $21_R$ for the right leg and a front end segment $21_L$ for the right leg. The front end segment $21_R$ is adapted to be held in close contact with the right leg of the wearer and the front end segment $21_L$ is adapted to be held in close contact with the left leg of the wearer wherein these front end segments $21_R$, $21_L$ describe a V-shape in FIG. 4. The rear end 22 also has its dimension in the transverse direction X bisected by the joint portion 35, in the same manner as the front end 21, into a rear end segment $22_R$ for the right leg and a rear end segment $22_L$ for the left leg. The rear end segment $22_R$ is adapted to be held in close contact with the right leg of the wearer and the rear end segment $22_L$ is adapted to be held in close contact with the left leg of the wearer wherein these rear end segments $21_R$, $21_L$ describe a V-shape in FIG. 4. The respective peripheries 13 of the leg-holes 12 in the absorbent chassis 10 comprise a periphery $13_R$ for the right leg and a periphery $13_L$ for the left leg wherein each of the peripheries $13_R$, $13_L$ is divided into an upper segment 15a free from the associated lateral edge 23 of the separator 20 and a lower segment 15b joined to the associated lateral edge 23 of the separator 20 (See FIG. 3 also). In FIG. 4, a range in which the upper segment 15a extends and a range in which the lower segment 15b extends are represented by double-headed arrows A and B, respectively.

A sequence in which the diaper of such configuration is put on the wearer and how the diaper 1 behaves in the course of being put on the wearer will be described. First, the front and rear waist regions 7, 8 of the absorbent chassis 10 is spaced apart from each other in the back-and-forth direction Y and thereby the waist-hole 11 is broadened as seen in FIGS. 1 and 4. Thereupon, the front end segment $21_R$ for the right leg and the front end segment $21_L$ for the left leg constituting the front end 21 of the separator 20 are deformed about the joint portion 35 so as to describe the V-shape and, in a similar way, the rear end segment $22_R$ for the right leg and the rear end segment $22_L$ for the left leg constituting the rear end 22 of the separator 20a are deformed so as to described the V-shape. Such deformation causes the front opening 33 and the rear opening 34 to be automatically broadened (See FIG. 3). At the same moment, the front end segment $21_R$ for the right leg and the rear end segment $22_R$ for the right leg are widely spaced apart from each other while the front end segment $21_L$ for the left leg and the rear end segment $22_L$ for the left leg are widely spaced apart from each other. Now the right leg of the wearer (not shown) is guided through an opening $41_R$ for the right leg defined by the upper segment 15a of the periphery segment $13_R$ of the associated leg-hole 12, the front end segment $21_R$ for the right leg of the separator 20a and the rear end segment $22_R$ for the right leg of the separator 20. The right leg is guided further through the right leg-hole 12 defined by the upper segment 15a and the lower segment 15b of the periphery segment $13_R$ for the right leg. Then the left leg is guided through an opening $41_L$ for the left leg defined by the upper segment 15a of the periphery segment $13_L$ for the left leg, the front end segment $21_L$ for the left leg and the rear end segment $22_L$ for the left leg. The left leg is guided further through the left leg-hole 12 defined by the upper segment 15a and the lower segment 15b of the periphery segment $13_L$ for the left leg.

In the diaper 1 put on the wearer in the manner as has been described above, the peripheries 13 of the respective leg-holes 12, i.e., the periphery $13_R$ for the right leg and the periphery $13_L$ for the left leg are elastically extensible and contractible around the respective holes 12 while the front end edge 21 and the rear end edge 22 of the separator 20 are elastically extensible and contractible in the transverse direction X. In a vicinity of the right groin, therefore, the upper segment 15a of the periphery $13_R$ for the right leg, the front end segment $21_R$ for the right leg and the rear end segment $22_R$ for the right leg are elastically held in close contact around the right leg to form a primary seal $51_R$ (See FIG. 4) serving to prevent leakage of body fluids from occurring around the right leg. Below a primary seal $51_R$, the lower segment 15b and the upper segment 15a of the periphery $13_R$ cooperate integrally with each other to form a secondary seal $52_R$ (See FIG. 4) serving to prevent leakage of body fluids from occurring around the right leg. This secondary seal $52_R$ functions in a similar manner to the manner in which the leg-surrounding seal in the conventional pants-type diaper function. Just as the case of the right leg, in a vicinity of the left groin, therefore, the upper segment 15a of the periphery $13_L$ for the left leg, the front end segment $21_L$ for the left leg and the rear end segment $22_L$ for the left leg are elastically held in close contact around the left leg to form a primary seal $51_L$. Below the primary seal $51_L$, the lower segment 15b and the upper segment 15b of the periphery $13_L$ cooperate integrally with each other to form a secondary seal $52_L$. The diaper put on the wearer may be sufficiently pulled up along the waist to ensure that the front end 21 and the rear end 22 of the separator 20, in a vicinity of the joint portion 35, come in contact with a zone of the wearer's crotch region defined between the wearer's external genital and anus. Even after the diaper 1 has been put on the wearer, the front end edge 21 as well as the rear end edge 22 of the separator 20 is maintained spaced apart from the bodyside liner 2 and the front opening 33 as well as the rear opening 34 is maintained widely broadened.

With the diaper 1 put on the wearer in this manner, the separator 20 distinctly separates the wearer's crotch region into a front half and a rear half so that the front opening 33 form in the front half is reliably opposed to the wearer's external genital and the rear opening 34 is reliably opposed to the anus. It is ensured, therefore, that urine discharged from the external genital is guided through the front opening 33 into the pocket-like bodily waste receiving space 31 while feces discharged from the anus is guided through the rear opening 34 into the bodily waste receiving space 31. In this way, the separator 20 effectively prevents urine and/or feces from coming in contact with the wearer's skin. A possibility that urine and feces might be mixed with each other within the bodily waste receiving space 31 is effectively alleviated because the separator 20 is substantially or really maintained in contact with the bodyside liner 2 at the bottom 6a of the crotch region 6. Consequentially, an anxiety that a liquidity of feces might be enhanced by admixture of urine and feces is effectively alleviated by the diaper 1. Even in the unlikely event that urine and/or feces is not guided into the bodily waste receiving space 31 but moves along the wearer's legs, the primary seals $51_R$, $51_L$ and the secondary seals $52_R$, $52_L$ provided around the wearer's legs cooperate together to prevent urine and/or feces from readily moving out beyond the leg-holes of the diaper 1.

The basic structure 10a of FIG. 2 further includes a pair of side flaps 25 defined by portions of the bodyside liner 2 and the outer sheet 3 extending outward in the transverse direction X beyond the lateral edges of the core 4. The side flaps 25 have a flexural stiffness in the transverse direction X lower than that of the core 4 and are correspondingly easier to be deformed. These side flaps 25 include the leg elastic portions 41. When the diaper 1 obtained from the basic structure 10a is in a state of FIG. 1 wherein the crotch region 6 bows in a U-shape, the side flaps 25 tend to raise themselves up along the lateral edges 4c of the core 4 under contraction of the elastic portions 41 in a vicinity of the transverse center line D-D, i.e., at the bottom 6a of the crotch region 6. On the other hand, the separator 20 is bonded along the lateral edges 23 thereof to the inner surface of the elastic portions 41 by means of adhesive 24. In response to deformation of the front and rear end edges 21, 22 of the separator 20 in a V-shape as shown in FIG. 4 from the state thereof shown in FIG. 2 wherein these front and rear end edges 21, 22 rectilinearly extend, these front and rear end edges 21, 22 function to pull the side flaps 25 toward the longitudinal center line C-C and thereby enhance the behavior of the side flaps 25 to raise themselves up. The side flaps 25 behaving in this manner are reliably held in close contact around the legs of the wearer from below and thereby effectively prevent leakage of body fluids from possibly occurring around the legs.

Figure 5:
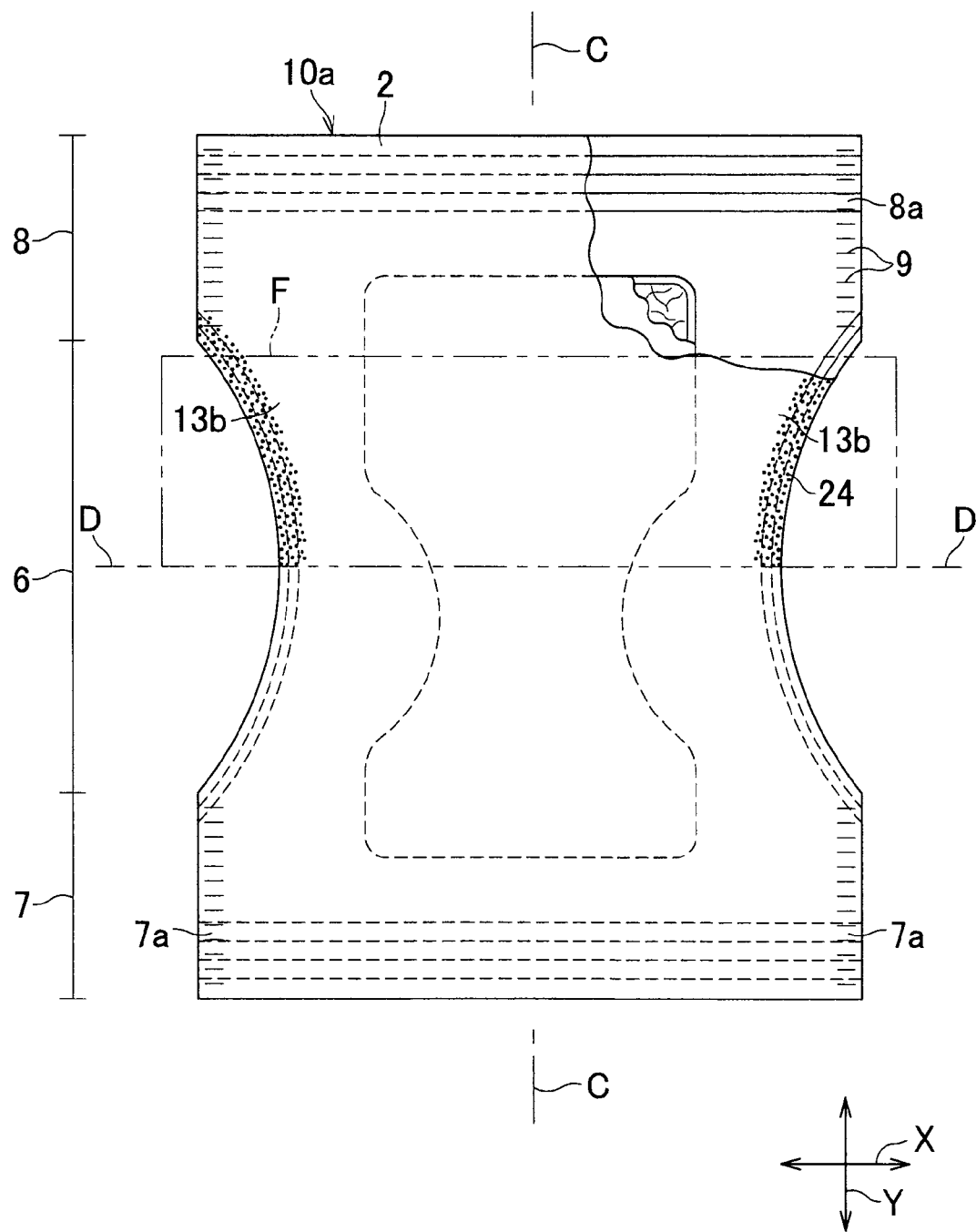
FIG. 5 is a plan view showing a basic structure as partially broken away.
Figure 6:
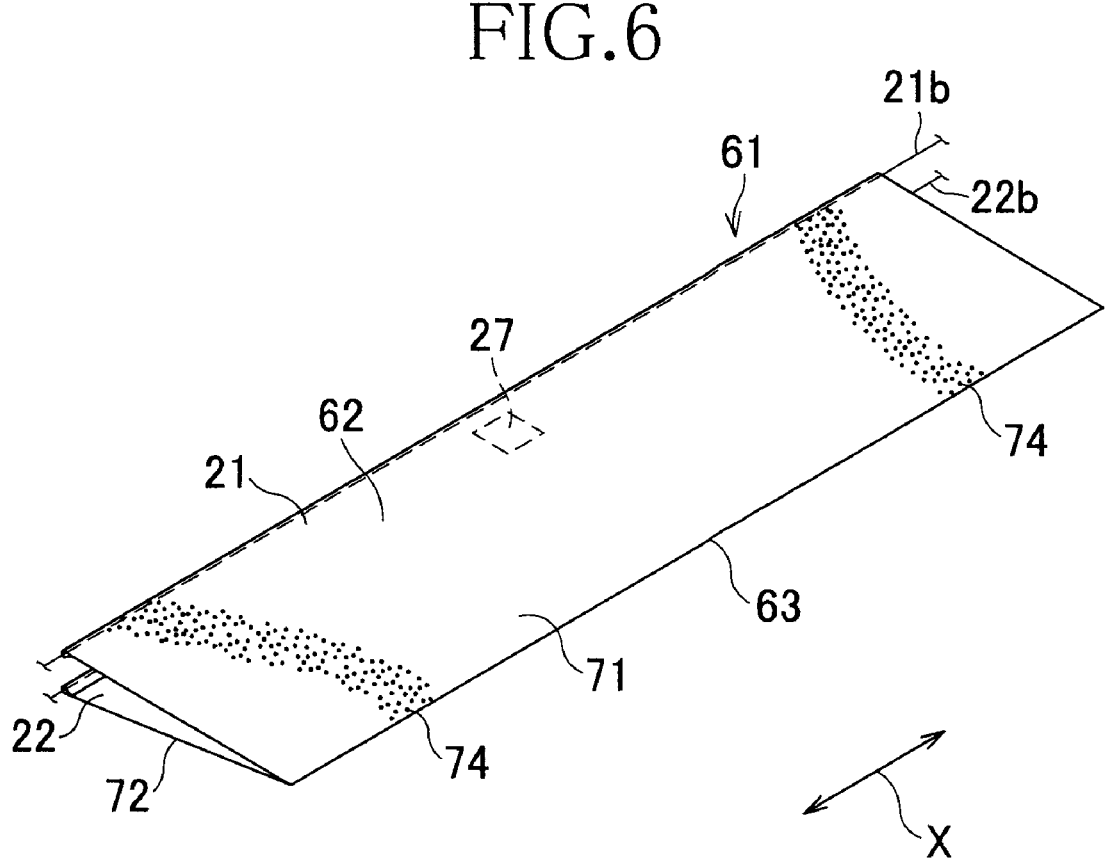
FIG. 6 is a perspective view of a folded sheet piece.

FIGS. 5 and 6 illustrate the steps to be followed to make the pants-type diaper 1 wherein FIG. 5 is a plan view of the basic structure 10a use to make the diaper 1 and FIG. 6 is a perspective view of a folded sheet piece 61 used to obtain the separator 20. In the basic structure 10a, the lateral edges 13b of the crotch region 6 are coated on the inner surface thereof with the adhesive 24 along at least segments of these edges 13b defined rearward from the transverse center line D-D. An imaginary line F indicated on the inner surface of the basic structure 10a indicates a region in which the folded sheet piece 61 is laid thereon. The folded sheet piece 61 is made of a sheet material 62 used to obtain the sheet piece 20a and the separator 20 formed by the sheet piece 20a and folded back along a fold line 63 so that front and rear end edges 21, 22 thereof are exactly placed upon each other. This folded sheet piece 61 is divided into a front half 71 and a rear half 72. The front and rear end edges 21, 22 are respectively provided with elastic members 21b, 22b attached, in respective states stretched in the transverse direction X, thereto and are bonded to each other in the joint portions 27, 28 (See FIG. 2) provided in the middle of these front and rear end edges 21, 22 as viewed in the transverse direction X by means of adhesions or sealing techniques. The front half 71 is to be bonded to the crotch region 6 of the basic structure 10a forwardly of the transverse center line D-D and, for this purpose, transversely opposite regions of the font half 71 are coated on the outer surface thereof with adhesive 74. The rear half 72 is to be bonded to the basic structure 10a in the rear of the transverse center line D-D by means of adhesive 24. A dimension in the transverse direction X of this folded sheet piece 61 is larger than a dimension in the transverse direction X of the section of the crotch region 6 upon which the folded sheet piece 61 is placed. The folded sheet piece 61 placed on the inner surface of the basic structure 10a occupies an area indicated by the imaginary line F.

The diaper 1 is obtained from this basic structure 10a in a manner as follows: first, the fold line 63 of the folded sheet piece 61 is brought close to the transverse center line D-D while the front and rear end edges 21, 22 are spaced farther than the fold line 63 from the transverse center line D-D. In this state, the rear half 72 is attached to the rear section of the crotch region 6 by means of adhesive 24 so that, between the lateral edges 13b of the crotch region 6, the front half 71 may be kept to be spaced apart from the basic structure 10a. Then the basic structure 10a is folded back along the transverse center line D-D so that the lateral edges 13b of the crotch region 6 are bonded to the front half 71 of the folded sheet piece 61 along sections of these edges 13b extending forwardly of the transverse center line D-D by means of adhesive 74 while, between the lateral edges 13b of the crotch region 6, the front half 71 is kept to be spaced apart from the basic structure 10a. The basic structure 10a folded back in this manner has the front and rear waist regions 7, 8 overlapped and bonded together at the joint spots 9 arranged along the lateral edges 7a, 7a; 8a, 8a of these waist regions 7, 8 so as to form the absorbent chassis 10. The folded sheet piece 61 partially extends beyond the lateral edges of this absorbent chassis 10 and such portion of the folded sheet piece 61 projecting from the absorbent chassis 10 may be cut off to trim the outline of the absorbent chassis 10 and thereby to obtain the diaper 1 having the separator 20. If desired, unnecessary portion of the absorbent chassis 10 also may be cut off together with these projecting portions of the folded sheet piece 61. For example, the peripheries 13 of the respective leg-holes 12 may be partially cut off to finish the diaper 1 in a desired shape.

In the diaper 1 obtained in this manner, the basic structure 10a defines the pants-shaped absorbent chassis 10 and the sheet piece 20a cooperates with the basic structure 10a to define the bodily waste receiving space 31 and at the same time to define the separator 20 (See FIG. 3) serving to prevent the wearer's skin from coming in contact with urine and feces. In the basic structure 10a of FIG. 2, the core 4 sandwiched between the bodyside liner 2 and the outer sheet 3 extends from the bottom 6a of the crotch region 6 in the back-and-forth direction Y preferably beyond the front end edge 21 and the rear end edge 22 of the separator 20 as seen in FIG. 2.

In the diaper 1 provided by the present invention, stock materials for the bodyside liner 2 may be selected from the group consisting of liquid-previous nonwoven fabrics and perforated plastic films. Stock materials for the outer sheet 3 may be selected from the group consisting of liquid-impervious plastic films and laminated sheets consisting of such plastic films and nonwoven fabrics. Liquid-absorbent materials for the core 4, a mixture of fluff pulp fibers and super-absorbent polymer particles, or fluff pulp fibers alone, or a mixture of fluff pulp fibers and super-absorbent polymer fibers may be used. For the wrapping sheet 4b, tissue paper often used may be replaced by appropriate nonwoven fabrics. As the sheet material 62 for the sheet piece 20a or the folded sheet piece 61, hydrophobic, or hydrophobic and liquid-impervious nonwoven fabrics or plastic films may be preferably used. More preferably, this sheet material 62 is elastically or inelastically extensible in response to elastic extension of the elastic members 21b, 22b. If the bodyside liner 2 and outer sheet 3 and the other sheet material such as the sheet material 62 contain any heat-fusible plastics, these sheet materials may be heat-sealed by means of sonic sealing techniques.

The preferred separator 20 according to the present invention is dimensioned so that the distance Hf from the transverse center line D-D to the front joint portion 27 is equal to the distance Hr from the transverse center line D-D to the rear joint portion 28. A preferred distance Hf, Hr in the diaper 1 for baby is in a range of 20 to 150 mm, more preferably in a range of 40 to 80 mm. In addition, a dimension of the front and rear joint portions 27, 28 in the transverse direction X is preferably in a range of 3 to 50 mm, more preferably in a range of 10 to 30 mm. A dimension of the separator 20 in the back-and-forth direction Y is at least 3 mm.

It is possible to use the folded sheet piece having a dimension in the transverse direction X smaller than the dimension of the crotch region 6 in the basic structure 10a of FIG. 5 instead of the folded sheet piece 61 used in the embodiment shown in FIG. 6 without departing from the scope of the invention. It is also possible without departing from the scope of the invention to bond the separator 20 obtained from the folded sheet piece 61 to the basic structure 10a in a vicinity of the transverse center line D-D.

While the method for making the disposable pants-type diaper 1 according to the present invention has been described hereinbefore with respect to several particular embodiments in which the method starts from the individual basic structure 10a and the individual folded sheet piece 61 attached thereto, the present invention is not limited to these particular embodiments. Without departing from the spirit and the scope of the invention, to obtain a series of the diapers 1 which are contiguous one to another in a web-like manner from a plurality of the basic structures 10a which are contiguous one to another in the transverse direction X or in the back-and-forth direction Y and a plurality of the folded sheet pieces 61 which are contiguous one to another in the transverse direction X or in the back-and-forth direction Y. In the latter case, the web-like series of the diapers 1 which are contiguous one to another may be cut into the individual diapers 1 in the final step.

The present invention makes it possible to obtain the disposable diaper facilitating the bodily waste receiving space of the diaper to be exactly opposed to the wearer's anus and protecting the wearer's skin from being soiled with urine and/or feces.

What is claimed is:

1. A disposable pants-type diaper comprising:
   a crotch region;
   a front waist region extending in a longitudinal direction of the diaper forward from said crotch region; and
   a rear waist region extending in the longitudinal direction rearward from said crotch region;
   wherein said front waist region and said rear waist region are joined together along respective lateral edges thereof so as to define an absorbent chassis;
   a separator on an inner surface of the chassis to protect a wearer's skin from contacting with feces discharged by the wearer;
   said separator comprising a piece of sheet extending in the longitudinal direction from said crotch region toward said front waist region as well as toward said rear waist region, extending across a longitudinal center line bisecting a width of said crotch region, and being fixed to said inner surface of said absorbent chassis on both sides of said longitudinal center line;
   wherein said sheet has
      a front end extending along a transverse direction of the diaper in the crotch region;
      a rear end extending along the transverse direction in the crotch region;
      side edges opposite to each other in the transverse direction in the crotch region and fixed to the absorbent chassis; and
      a middle zone provided between the front end and the rear end in the longitudinal direction and between the side edges in the transverse direction, said middle zone being free from direct attachment to said inner surface of said absorbent chassis so that a bodily waste receiving space is formed between the separator and the inner surface,
   wherein the front and rear ends of the separator are directly attached to each other at respective joint regions thereof,
   wherein the bodily waste receiving space defined by the separator and the inner surface has
   a front opening defined by the front end together with the inner surface; and
   a rear opening defined by the rear end together with the inner surface.

2. The diaper as defined by claim 1, wherein
   said crotch region has lateral edges extending in the longitudinal direction of said diaper,
   said lateral edges respectively defining leg-holes and being provided with leg-encircling elastic members attached in a stretched state thereto so as to define leg-encircling elastic zones adapted to be stretchable/contractible in a circumferential direction around each of said leg-holes and
      wherein said front end as well as said rear end of said separator extend to said lateral edges and are joined to said inner surface of said absorbent chassis in said leg-encircling elastic zones.

3. The diaper as defined by claim 1, wherein
   said crotch region has lateral edges extending in the longitudinal direction of said diaper,
   said lateral edges respectively defining leg-holes and being provided with leg-encircling elastic members attached in a stretched state thereto so as to define leg-encircling elastic zones adapted to be stretchable/contractible in a circumferential direction around each of said leg-holes and
   wherein said front end as well as said rear end of said separator extend to said lateral edges and are joined to said inner surface of said absorbent chassis at points placed inwardly, in the transverse direction, from said leg-encircling elastic zones toward said longitudinal center line.

4. The diaper as defined by claim 1, wherein said separator further comprises a front elastic member and a rear elastic member, which define a front elastic portion and a rear elastic portion including the front end and the rear end, respectively, and extending between the lateral edges of the crotch region,
   wherein said front elastic region and said rear elastic region are stretchable/contractible in said transverse direction.

5. The diaper as defined by claim 1, wherein said front waist region and said rear waist region are permanently directly bonded together at a plurality of joint spots intermittently arranged along the lateral edges of the front and rear waist regions.

6. The diaper as defined by claim 1, wherein said crotch region comprises,
   lateral edges respectively defining leg-holes and being provided with leg-encircling elastic members attached in a stretched state thereto so as to define leg-encircling elastic zones being stretchable/contractible in a circumferential direction around each of said leg-holes;
   a body fluid absorbent core containing at least one of fluff pulp and super-absorbent polymer particles and, on both sides of said absorbent core; and
   flaps each containing at least one of a nonwoven fabric and a plastic film and having a flexural stiffness lower than that of said absorbent core, wherein said leg-encircling elastic zones are formed in said flaps, respectively.

7. The diaper as defined by claim 1, wherein the piece of sheet is hydrophobic.

8. The diaper as defined by claim 1, wherein the front end and the rear end of the separator have a shorter dimension in the transverse direction than that said crotch region.

9. The diaper as defined by claim 1, wherein said joint regions of the separator are permanently directly bonded to each other by a bond.

10. The diaper as defined by claim 9, wherein said bond is hot melt adhesive or pressure-sensitive adhesive.

* * * * *